(12) United States Patent
Li

(10) Patent No.: US 9,987,090 B2
(45) Date of Patent: Jun. 5, 2018

(54) LASER ASSEMBLY HAVING ADJUSTABLE FOCUSING LENSES

(75) Inventor: Jamie Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1057 days.

(21) Appl. No.: 13/327,625

(22) Filed: Dec. 15, 2011

(65) Prior Publication Data

US 2012/0157979 A1 Jun. 21, 2012

Related U.S. Application Data

(60) Provisional application No. 61/424,014, filed on Dec. 16, 2010.

(51) Int. Cl.
| | |
|---|---|
| A61B 18/18 | (2006.01) |
| A61B 18/24 | (2006.01) |
| A61B 18/22 | (2006.01) |

(52) U.S. Cl.
CPC ............ *A61B 18/24* (2013.01); *A61B 18/245* (2013.01); *A61B 2018/2266* (2013.01); *A61B 2218/001* (2013.01)

(58) Field of Classification Search
CPC .. A61B 1/04; A61B 1/12; A61B 18/18; A61B 17/10; A61D 1/00; A61C 1/00; G02B 1/06

USPC ........ 356/345, 346, 351; 600/109, 128, 157; 606/15, 140, 219; 433/29; 359/665

See application file for complete search history.

(56) References Cited

U.S. PATENT DOCUMENTS

| | | | | |
|---|---|---|---|---|
| 5,199,417 | A * | 4/1993 | Muller et al. | 600/128 |
| 5,321,501 | A * | 6/1994 | Swanson et al. | 356/479 |
| 5,575,756 | A * | 11/1996 | Karasawa et al. | 600/157 |
| 6,099,535 | A * | 8/2000 | Lamport et al. | 606/140 |
| 6,445,939 | B1 * | 9/2002 | Swanson et al. | 600/342 |
| 7,156,863 | B2 * | 1/2007 | Sonnenschein et al. | 606/219 |
| 7,233,820 | B2 * | 6/2007 | Gilboa | 600/427 |
| 7,359,124 | B1 * | 4/2008 | Fang | G02B 1/06 359/665 |
| 2004/0106081 | A1 * | 6/2004 | Karazivan et al. | 433/29 |
| 2008/0108869 | A1 * | 5/2008 | Sanders et al. | 600/109 |

* cited by examiner

*Primary Examiner* — Aaron Roane
(74) *Attorney, Agent, or Firm* — Bookoff McAndrews, PLLC

(57) ABSTRACT

Embodiments of the disclosure may include an apparatus including an optical fiber having a distal end and configured to emit a beam of energy. The apparatus may also include a first lens coupled to the distal end of the optical fiber and a sheath including a channel and a second lens positioned on a distal region of the sheath. The optical fiber may be disposed within the channel of the sheath to permit relative movement between the first lens and the second lens and thereby adjust a beam of energy that exits the sheath.

16 Claims, 2 Drawing Sheets

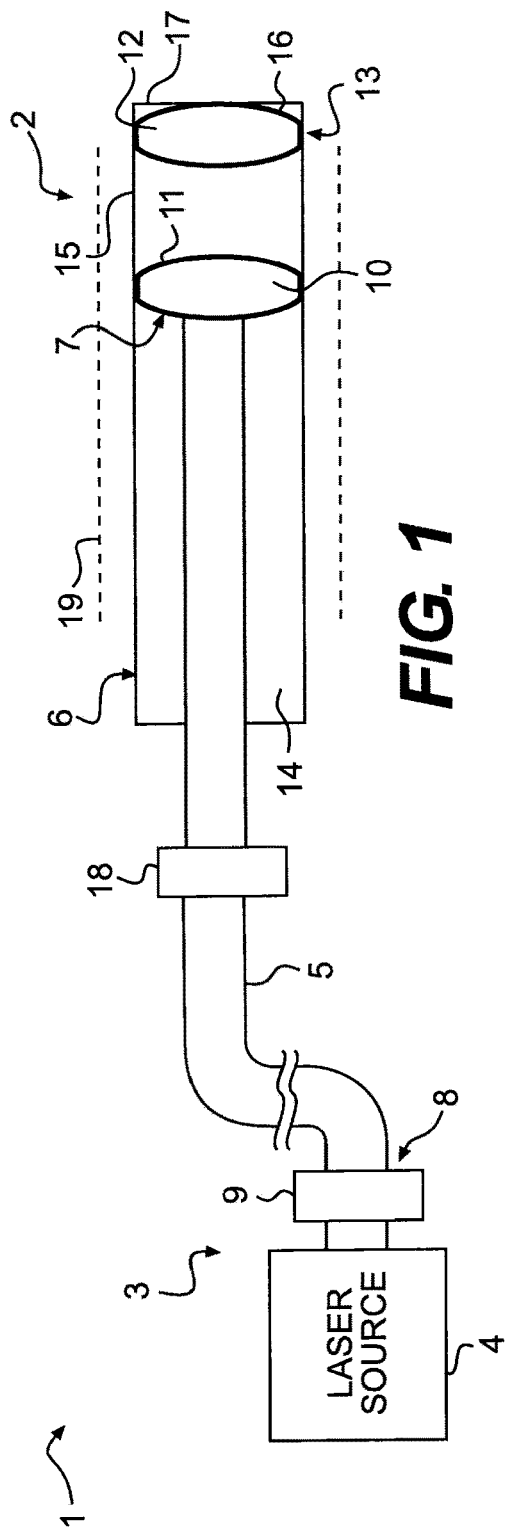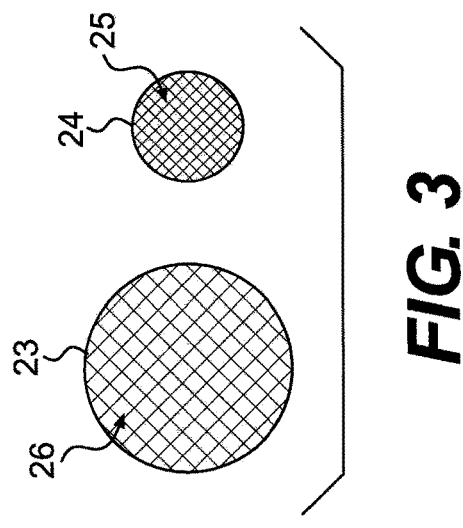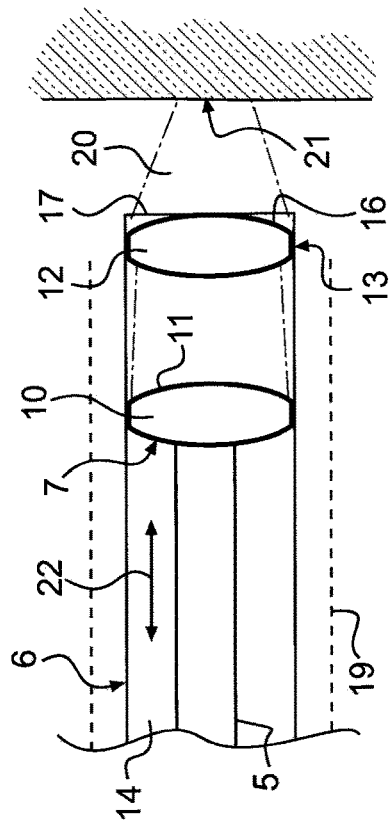

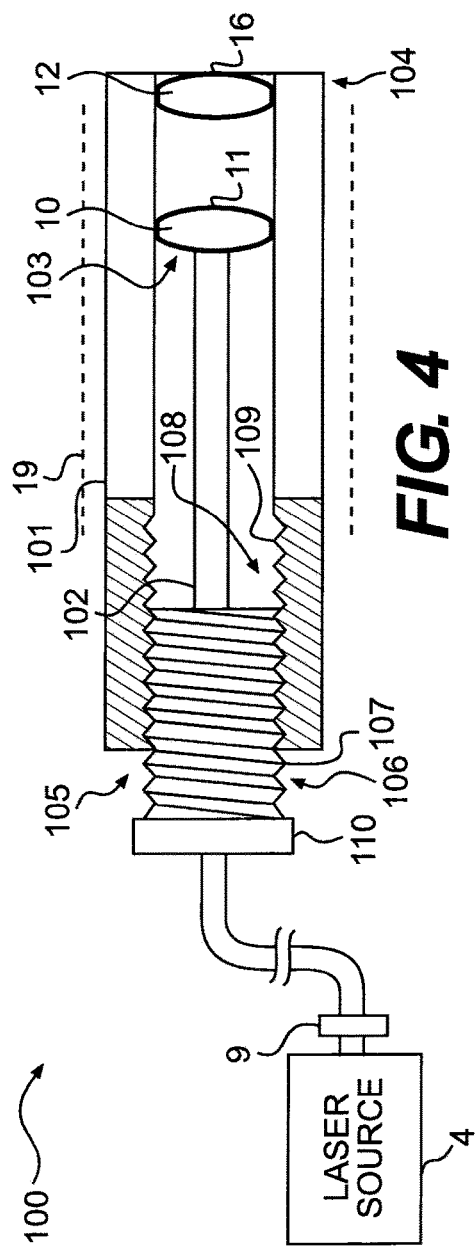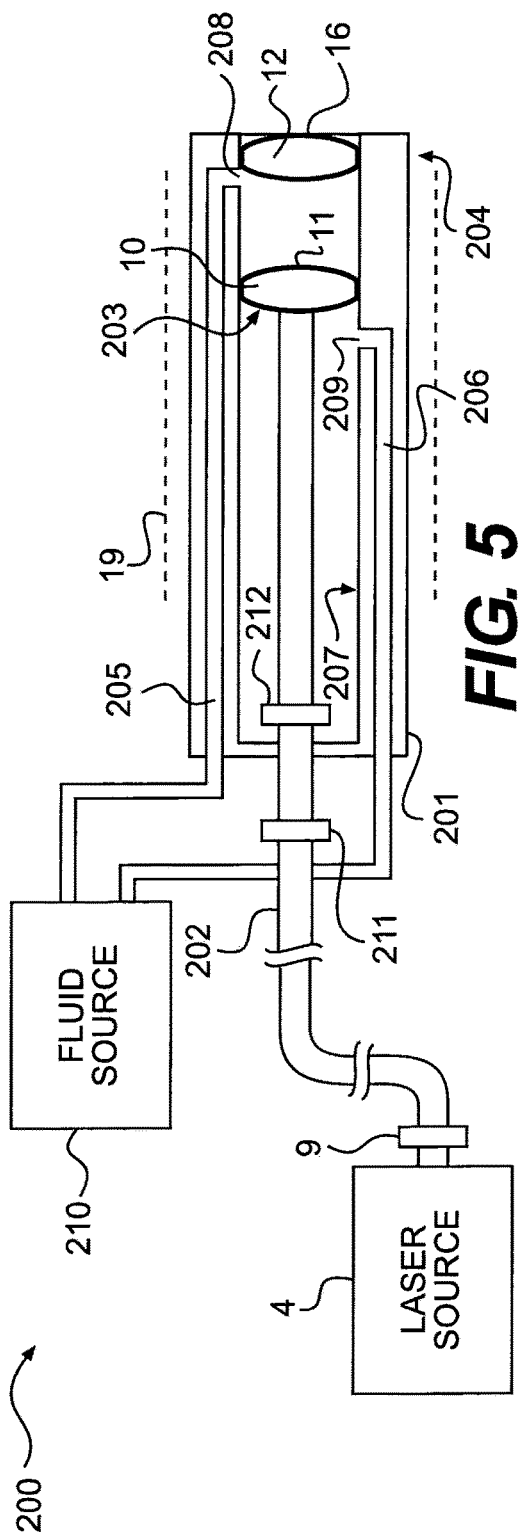

LASER ASSEMBLY HAVING ADJUSTABLE FOCUSING LENSES

CROSS REFERENCE TO RELATED APPLICATION

This patent application claims the benefit of priority under 35 U.S.C. §§ 119 and 120 to U.S. Provisional Patent Application No. 61/424,014, filed Dec. 16, 2010, which is incorporated herein by reference in its entirety.

FIELD OF THE DISCLOSURE

Embodiments of the present disclosure include medical devices, and more particularly, medical devices including a laser assembly with adjustable focusing lenses and related methods of using such medical devices

BACKGROUND OF THE DISCLOSURE

Generally speaking, laser assemblies may be used for laser-based surgical procedures to, for example, deliver laser energy to fragment or vaporize body tissue or foreign matter, such as kidney stones, other calculi, and/or fragments thereof. A conventional laser assembly may include an optical fiber coupled to a laser energy source. The laser assembly may be configured to transmit laser energy from the laser energy source to a target treatment area of a patient's body. Particularly, a beam of laser energy may be outputted through a distal end of the optical fiber. In some instances, the laser energy outputted from the optical fiber may be adjusted via the laser energy source. For example, a user may actuate various power controls on the laser energy source to increase or decrease the intensity of the outputted laser energy. Moreover, it may be desirable to adjust the laser beam size based on the size of the target treatment area. For instance, a smaller beam of laser energy may be appropriate to treat a smaller area of target tissue, and a larger beam of laser energy may be appropriate to treat a larger area of target tissue. Typically, the laser beam size may correspond to the diameter of the optical fiber. Therefore, when encountering variations in treatment area size, a user may manually switch between appropriately sized optical fibers.

Adjusting the intensity on the laser energy source and changing optical fibers, however, are time consuming and cumbersome. Accordingly, a need exists to simplify the manner in which the intensity and the size of the outputted laser energy are adjusted. The laser assemblies and related methods of the present disclosure are directed to improvements in the existing technology.

SUMMARY OF THE DISCLOSURE

In accordance with an embodiment, an apparatus may include an optical fiber including a distal end and configured to emit a beam of energy. The apparatus may also include a first lens coupled to the distal end of the optical fiber and a sheath including a channel and a second lens positioned on a distal region of the sheath. The optical fiber may be disposed within the channel of the sheath to permit relative movement between the first lens and the second lens and thereby adjust a beam of energy that exits the sheath.

Various embodiments of the disclosure may include one or more of the following aspects: the optical fiber may be slidably disposed within the channel; the first lens and the second lens may be arranged so that the beam of energy may pass through the first lens and the second lens before exiting the distal region of the sheath; an intensity of the beam of energy that exits the distal region of the sheath may increase when a distance between the first lens and the second lens increases, and the intensity of the beam of energy may decrease when the distance between the first lens and the second lens decreases; a spot size of the beam of energy that exits the distal region of the sheath may increase when a distance between the first lens and the second lens decreases, and the spot size may decrease when the distance between the first lens and the second lens increases; the first lens may be fixedly attached to the distal end of the optical fiber, and the second lens may be fixedly attached within the channel of the sheath; a stop may be coupled to the optical fiber and positioned external the channel of the sheath, wherein the stop may be configured to limit distal advancement of the optical fiber; the stop may be positioned such that the first and second lenses are prevented from contacting each other; a proximal portion of the optical fiber may include a plurality of first threads, and a proximal portion of the sheath may include a plurality of second threads mating with the plurality of first threads; the plurality of first threads and the plurality of second threads may be coupled such that relative rotation of the optical fiber and the sheath longitudinally moves the optical fiber relative to the sheath; the sheath may include a first fluid delivery channel and a second fluid delivery channel; an opening of the first fluid delivery channel may be positioned between the first and second lenses, and an opening of the second fluid delivery channel may be positioned proximal the first lens; fluid delivery to the first fluid delivery channel may proximally retract the optical fiber, and fluid delivery to the second fluid delivery channel may distally advance the optical fiber; the apparatus may be a medical device; and the optical fiber and the sheath may be flexible to traverse a tortuous anatomy in a body.

In accordance with another embodiment, a method of transmitting a beam of energy from an apparatus having an optical fiber disposed within a sheath may include transmitting a beam of energy through the optical fiber and through a first lens coupled to a distal end of the optical fiber. The method may also include emitting the beam of energy out of the sheath through a second lens positioned on a distal region of the sheath and adjusting the beam of energy that exits the sheath by moving the first lens relative to the second lens.

Various embodiments of the disclosure may include one or more of the following aspects: increasing an intensity of the beam of energy that exits the sheath by increasing a distance between the first lens and the second lens, and decreasing the intensity of the beam by decreasing the distance between the first lens and the second lens; a spot size of the beam of energy that exits the sheath may increase when a distance between the first lens and the second lens decreases, and the spot size may decrease when the distance between the first and second lenses increases; moving the first lens and the second lens relative to each other may include longitudinally translating the optical fiber relative to the sheath; and directing the beam of energy from the apparatus towards tissue of a patient.

In this respect, before explaining at least one embodiment of the present disclosure in detail, it is to be understood that the present disclosure is not limited in its application to the details of construction and to the arrangements of the components set forth in the following description or illustrated in the drawings. The present disclosure is capable of embodiments in addition to those described and of being practiced and carried out in various ways. Also, it is to be understood that the phraseology and terminology employed herein, as well as the abstract, are for the purpose of description and should not be regarded as limiting.

The accompanying drawings illustrate certain exemplary embodiments of the present disclosure, and together with the description, serve to explain the principles of the present disclosure. As such, those skilled in the art will appreciate that the conception upon which this disclosure is based may readily be used as a basis for designing other structures, methods, and systems for carrying out the several purposes of the present disclosure. It is important, therefore, to recognize that the claims should be regarded as including such equivalent constructions insofar as they do not depart from the spirit and scope of the present disclosure.

BRIEF DESCRIPTION OF THE DRAWINGS

FIG. 1 illustrates a schematic view of a laser assembly, according to an exemplary disclosed embodiment;

FIG. 2 illustrates a schematic view of a distal end portion of the laser assembly of FIG. 1, according to an exemplary disclosed embodiment;

FIG. 3 illustrates a comparative depiction between spot sizes emitted from the laser assembly of FIG. 1, according to an exemplary disclosed embodiment;

FIG. 4 illustrates a schematic view of another laser assembly, according to an exemplary disclosed embodiment; and FIG. 5 illustrates a schematic view of another laser assembly, according to an exemplary disclosed embodiment.

DETAILED DESCRIPTION

Reference will now be made in detail to the exemplary embodiments of the present disclosure described above and illustrated in the accompanying drawings.

The terms "proximal" and "distal" are used herein to refer to the relative positions of the components of an exemplary laser assembly. When used herein, "proximal" refers to a position relatively closer to the exterior of the body or closer to the surgeon, or other user, using the laser assembly. In contrast, "distal" refers to a position relatively further away from the surgeon, or other user, using the laser assembly or closer to the interior of the body.

The present disclosure relates to laser assemblies having adjustable focusing lenses. Particularly, the adjustable focusing lenses may adjust a size and/or an intensity of a laser beam emitted from a laser assembly. In general, a first focusing lens may be aligned with a second focusing lens, and the laser beam may be emitted through the first and second focusing lenses. The first and second focusing lenses may be moved relative to each other to alter the size and/or the intensity of the emitted laser beam. In one embodiment, as will be discussed below, the first focusing lens may be positioned on an optical fiber, and the second focusing lens may be positioned within a distal end of a sheath. The optical fiber may be disposed within and axially move relative to the sheath, thereby effectuating the relative movement between the first and second focusing lenses.

FIG. 1 illustrates a schematic drawing of laser assembly 1 according to an exemplary embodiment. The laser assembly 1 may include a distal end portion 2 and a proximal end portion 3. The laser assembly 1 may also include a laser source 4, an optical fiber 5, and a sheath 6. The laser source 4 may be located in the proximal end portion 3 of the laser assembly 1, and the optical fiber 5 may extend between the proximal and distal end portions 3, 2 of the laser assembly 1 and may be slidably disposed within the sheath 6. The laser assembly 1 may be used to transmit laser energy from the laser source 4 to a target treatment area within a patient's body, through, for example, the distal end portion 2 of the laser assembly 1.

The laser source 4 may include at least one laser that may be used to generate laser energy for surgical procedures. The laser source 4 may include at least one of, for example, a Ho:YAG laser, a neodymium-doped:YAG (Nd:YAG) laser, a semiconductor laser diode, or a potassium-titanyl phosphate crystal (KTP) laser. The laser source 4 may include more than one laser, and more than one laser may be used during a surgical procedure. The laser source 4 may also include a processor that provides timing, wavelength, and/or power control of the laser(s). For example, the laser source 4 may include one or more mechanisms for laser selection, filtering, temperature compensation, and/or Q-switching operations.

The optical fiber 5 may include a distal end 7 and a proximal end 8. The proximal end 8 of the optical fiber 5 may be coupled to the laser source 4 in the proximal end portion 3 of the laser assembly 1. For example, the proximal end 8 of the optical fiber 5 may be coupled to the laser source 4 through an optical coupler 9 in or near the proximal end portion 3 of the laser assembly 1. The optical coupler 9 may be, for example, an SMA (SubMiniature version A) connector. The proximal end 8 of the optical fiber 5 may be configured to receive laser energy from the laser source 4 via the optical coupler 9, and the optical fiber 5 may be configured to output the laser energy through the distal end 7 of the optical fiber 5.

The optical fiber 5 may include, for example, a core, one or more cladding layers about the core, a buffer layer about the cladding, a jacket, etc. The core may be made of a suitable material for the transmission of laser energy from the laser source 4. The core may be multi-mode and may have a step or graded index profile. The cladding may be a single or a double cladding that may be made of a hard polymer or silica. The buffer may be made of a hard polymer such as Tefzel®, for example. When the optical fiber 5 includes a jacket, the jacket may be made of Tefzel®, for example, or other polymers. The optical fiber 5 may be made of a suitable biocompatible material and may be flexible, for example, to traverse tortuous anatomy in the body.

The optical fiber 5 may also include a first lens 10 fixedly attached to the distal end 7 of the optical fiber 5. The first lens 10 may be configured to focus and sharpen the output of laser energy from the distal end 7 of the optical fiber 5. The first lens 10 may include, for example, any suitable laser focus lens, including a biconvex focusing lens (as shown in FIG. 1) or a planoconvex focusing lens, such that a beam of laser energy emitted from the optical fiber 5 may be sharpened and focused as the beam exits a distal facing end 11 of the first lens 10.

The sheath 6 may be formed from, for example, a rod, tube, cannula, stent or other cylindrical structures. The sheath 6 may also be made from a flat sheet of any material known in the art that is formed into a cylindrical shape. Furthermore, the sheath 6 may be made of a suitable biocompatible material and may be flexible, for example, to traverse tortuous anatomy in the body. A second lens 12 may be positioned on a distal region 13 of the sheath 6. The second lens 12 may be disposed within a channel 14 of the sheath 6 and may be fixedly attached to a wall 15 of the channel 14. In one embodiment, a distal facing end 16 of the second lens 12 may be flush with a distal face 17 of the sheath 6. Alternatively, the second lens 12 may be mounted in a more proximal position within the channel 14. Similar to the first lens 10, the second lens 12 may be configured to focus and sharpen the output of laser energy from the distal facing end 11 of the first lens 10. The second lens 12 may include, for example, any suitable laser focus lens, including a biconvex focusing lens (as shown in FIG. 1) or a plano-convex focusing lens, such that the focused beam of laser energy emitted from the first lens 10 may be further sharpened and focused as the beam exits the distal facing end 16 of the second lens 12. It should also be appreciated that the first and second lenses 10, 12 may be the same or different type of focusing lens.

It should be appreciated that the first lens 10 and the second lens 12 may be made of any suitable material known in the art capable of passing a laser beam with minimal loss of energy, such as glass, diamond, or polymeric materials. Moreover, each of the first lens 10 and the second lens 12 may include a lens assembly comprising of a plurality of focusing lenses.

The optical fiber 5 may be slidably disposed within the channel 14 of the sheath, and accordingly, the sheath 6 and the optical fiber 5 may longitudinally slide relative to each other. The first lens 10 may be appropriately sized such that the optical fiber 5 may slidably move relative to the sheath 6, yet secure the optical fiber 5 to the sheath 6 when the optical fiber 5 is stationary. For example, the first lens 10 may include a diameter approximately the same or slightly smaller than a diameter of the channel 14. In another embodiment, laser assembly 1 may include a locking mechanism configured to restrain the movement of the optical fiber 5 relative to the sheath 6. For example, the sheath 6 may include a spring-loaded protrusion or a button-like apparatus configured to engage and fix the optical fiber 5 from movement. Moreover, in certain embodiments, the diameter of the optical fiber 5 may be approximately the same as the diameter of the first lens 10 and the diameter of the second lens 12.

It should also be appreciated that the laser assembly 1 may include any suitable handle coupled to either the sheath 6 or the optical fiber 5 to permit relative axial movement between the sheath 6 and the optical fiber 5. In other embodiments, axial movement between the sheath 6 and the optical fiber 5 may be effectuated without a handle (i.e., the sheath 6 and/or the optical fiber 5 may not be coupled to a handle).

Distal advancement of the optical fiber 5 relative to the sheath 6 may be limited by a hard stop 18 coupled to the optical fiber 5 and positioned external the channel 14 of the sheath 6. The hard stop 18 may have a diameter larger than an opening of the channel 14, and therefore, may inhibit distal advancement of optical fiber 5 into the channel 14. The position of the hard stop 18 may correspond to a predetermined distance that prevents damage to the optical fiber 5 and the first and second lenses 10, 12. For example, the hard stop 18 may be positioned such that the first and second lenses 10, 12 may be prevented from contacting each other when the optical fiber 5 is distally advanced. In another embodiment, hard stops may be positioned within the channel 14 to limit distal advancement of the optical fiber 5. For example, a first hard stop may be coupled to the optical fiber 5 and positioned within the channel 14, and a second hard stop may be coupled to the channel 14 and positioned distal the first hard stop, so that the first hard stop cannot move distal to the second hard stop.

The laser assembly 1 may be of a suitable size to extend within a catheter or endoscope 19 for inserting the distal end portion 2 of the laser assembly 1 into a patient's body. The endoscope 19 may define one or more lumens. In some embodiments, the endoscope 19 may include a single lumen that may receive various components such as the distal end portion 2 of the laser assembly 1. The endoscope 19 may have a proximal end configured to receive the distal end portion 2 of the laser assembly 1 and a distal end configured to be inserted into a patient's body for positioning the distal end portion 2 of the laser assembly 1 in an appropriate location for a laser-based surgical procedure. For example, to perform a surgical procedure near the prostate, the endoscope 19 may be used to place the distal end portion 2 of the laser assembly 1 at or near the prostate gland. The endoscope 19 may be made of a suitable biocompatible material and may include an elongate portion that may be flexible to allow the elongate portion to be maneuvered within the body. The endoscope 19 may also be configured to receive various other medical devices or tools through one or more lumens of the endoscope 19, such as, for example, irrigation and/or suction devices, forceps, drills, snares, needles, etc. In some embodiments, the endoscope 19 may include a fluid channel (not shown) coupled at a proximal end to a fluid source (not shown). The fluid channel may be used to irrigate an interior of the patient's body during a laser-based surgical procedure. In some embodiments, the endoscope 19 may include an optical device (not shown), e.g., including an eyepiece coupled to a proximal end of the endoscope 19. The optical device may include an optical fiber or other image transmission device, e.g., a wireless device, that may be disposed in or on the endoscope 19, e.g., in a lumen or on a distal end of the endoscope 19, to transmit an image signal to the surgeon. Such an embodiment allows a medical practitioner to view the interior of a patient's body through the eyepiece.

FIG. 2 illustrates the distal end portion 2 of the laser assembly 1, according to an exemplary embodiment.

An optical beam, for example, a laser beam 20 including laser energy may be transmitted from the laser source 4, through the optical fiber 5 from its proximal end 8 to its distal end 7, and then through the first lens 10. The laser beam 20 emitted from the first lens 10 may then exit the sheath 6 through the second lens 12 and to a patient's treatment area 21. The laser beam 20 may exit the sheath 6 generally parallel to a longitudinal axis of the sheath 6.

As the laser beam 20 is transmitted through the first lens 10 and the second lens 12 in reaching the treatment area 21, the diameter (i.e., the spot size) of the laser beam 20 and the intensity of the laser energy associated with the laser beam 20 may be adjusted by altering a distance between the first and second lenses 10, 12. Because the first lens 10 and the second lens 12 form a compound lens system of two converging lenses (i.e., focusing lenses), the laser beam 20 may become more focused, and therefore the laser energy may become more intense, as the distance between the first lens 10 and the second lens 12 increases. Moreover, as the distance between the first and second lenses 10, 12 increases, the laser beam 20 emitted from the sheath 6 may increasingly converge, such that the spot size of the laser beam 20 becomes smaller. Conversely, decreasing the distance between the first and second lenses 10, 12 may decrease the intensity of the laser energy emitted from the sheath 6, in addition to increasing the spot size of the laser beam 20. The intensity and the spot size of the laser beam 20 may be determined by known laws and principles associated with, for example, lasers and lenses. For instance, lens characteristics, such as focal length and separation distances between multiple lenses, may be factors in determining spot size and intensity.

The distance between the first and second lenses 10, 12 may be altered by relative movement between the optical fiber 5 and the sheath 6. In one embodiment, for example, the sheath 6 may be distally advanced to increase the distance between the first and second lenses 10, 12, and may be proximally retracted to decrease the distance between the first and second lenses 10, 12, as depicted by double-headed arrow 22. In another embodiment, the optical fiber 5 may be distally advanced or proximally retracted, while the sheath 6 is kept stationary.

Accordingly, since the intensity of the laser energy and the spot size of the laser beam 20 may be modified by merely adjusting the distance between the first and second lenses 10, 12, the laser energy produced by the laser source 4 may be maintained at a constant magnitude. That is, the laser assembly 1 may eliminate the need for a user to manually adjust the controls on the laser source 4 when increased or decreased laser energy at a treatment site is desired. In addition, the laser assembly 1 may eliminate the need to manually switch between larger and smaller diameter optical fibers to adjust the spot size of the laser beam 20. However, it should be appreciated that a user may also actuate the controls of the laser source 4 when desired. For example, the user may increase the spot size of the laser beam by relative movement between the sheath 6 and the optical fiber 5 and then increase the intensity output of the laser beam via the laser source 4, thereby producing a high intensity, large spot size laser beam.

FIG. 3 illustrates a comparison between exemplary spot sizes associated with the laser beam 20. As discussed above, increasing the distance between the first and second lenses 10, 12 decreases the spot size of the laser beam emitted from the sheath 6, and decreasing the distance between the first and second lenses 10, 12 increases the spot size. As such, a larger spot size 23 may correspond to the laser beam 20 when the first and second lenses 10, 12 are closer together, as compared to a smaller spot size 24 which may correspond to the laser beam 20 when the first and second lenses 10, 12 are farther apart. The larger spot size 23 of the laser beam 20 may be appropriate for treating a larger treatment area, whereas the smaller spot size 24 of the laser beam 20 may be appropriate for treating a smaller treatment area.

Furthermore, the smaller spot size 24 may have a higher energy density 25 (illustrated as cross-hatching) as compared to an energy density 26 (illustrated as cross-hatching) of the larger spot size 23. Accordingly, the higher energy density 25 of the smaller spot size 24 may be appropriate for applications which may require a higher intensity of laser energy, such as, for example, breaking up calculi and other hard foreign matters.

It should be appreciated that the spot sizes 23, 24 are intended for illustrative purposes only and do not necessarily depict accurate dimensions of spot sizes emitted from the disclosed laser assembly 1. It should also be appreciated that smaller spot size 24 may be approximately one tenth the size of the diameter of the optical fiber 5, and larger spot size 24 may be approximately five times the diameter of the optical fiber 5.

FIG. 4 illustrates another embodiment of a laser assembly 100. Laser assembly 100 may include a sheath 101 and an optical fiber 102. Optical fiber 102 may be coupled to the laser source 4 via the optical coupler 9. Similar to the embodiment of FIG. 1, the first lens 10 may be fixedly attached to a distal end 103 of the optical fiber 102, and the second lens 12 may be positioned on a distal region 104 of the sheath 101. The laser assembly 100 may also include a positioning mechanism 105 for moving and setting a relative position between the sheath 101 and the optical fiber 102. The positioning mechanism 105 may include, for example, a threaded screw-nut configuration. In other words, a proximal portion 106 of the optical fiber 102 may include a plurality of external threads 107, and a proximal portion 108 of the sheath 101 may include a plurality of internal threads 109. The plurality of external threads 107 and the plurality of internal threads 109 may be coupled such that relative rotation of the optical fiber 102 and the sheath 101 may be converted to relative linear movement between the optical fiber 102 and the sheath 101. For example, a user may turn the sheath 101 in a clockwise or counterclockwise direction to advance or retract the optical fiber 102 relative to the sheath 101. Such relative linear movement may alter the relative position between the first lens 10 and the second lens 12. In addition, the proximal portion 106 of the optical fiber 102 may include a hard stop 110 configured to prevent distal advancement of the optical fiber 102 beyond a predetermined distance.

The positioning mechanism 105 may provide improved precision in positioning the first lens 10 relative to the second lens 12. Particularly, the relative movement between the optical fiber 102 and the sheath 101 (and thus the relative position between the first and second lenses 10, 12) may be incrementally adjusted by rotating either the optical fiber 102 or the sheath 101, thereby, accurately modifying a desired spot size and energy density of a laser beam emitted from the laser assembly 100. It should also be appreciated that the external threads 107 of the optical fiber 102 may include, for example, markings, notches, or the like, to indicate to a user a corresponding spot size or intensity of the laser beam. For instance, spot sizes and/or intensities of the laser beam may be labeled on external threads 107 such that a user may know the spot size and/or intensity of the emitted laser beam as the user incrementally rotates the sheath 102 relative to the optical fiber 101. Accordingly, the user may accurately adjust between known laser spot sizes and/or intensities external the patient. Similarly, and with respect to the embodiment of FIG. 1, the outer surface of the optical fiber 5 may also include for example, markings, notches, or the like, to indicate to a user a corresponding spot size or intensity of the laser beam.

FIG. 5 illustrates another embodiment of a laser assembly 200. The laser assembly 200 may include a sheath 201 and an optical fiber 202 slidably disposed within the sheath 201. Optical fiber 202 may be coupled to the laser source 4 via the optical coupler 9. Similar to the embodiment of FIG. 1, the first lens 10 may be fixedly attached to a distal end 203 of the optical fiber 202, and the second lens 12 may be positioned on a distal region 204 of the sheath 201.

The sheath 201 may include a first fluid delivery channel 205 and a second fluid delivery channel 206, each formed in a wall 207 of the sheath 201. In another embodiment, the first and second fluid delivery channels 205, 206 may be separate conduits positioned on the wall 207 and within the sheath 201. The first fluid delivery channel 205 and the second fluid delivery channel 206 may be separate channels, that is, the channels 205, 206 may not be in fluid communication with each other. Moreover, the first fluid delivery channel 205 may include a first outlet 208 positioned between the first and second lenses 10, 12 (i.e., distal the first lens 10 and proximal the second lens 12). The second fluid delivery channel 206 may include a second outlet 209 proximal to both the first and second lenses 10, 12.

A fluid source 210 may be in communication with the first and second fluid delivery channels 205, 206 and may individually deliver a fluid, such as saline or an inert gas, to each of the first and second fluid delivery channels 205, 206. Accordingly, a user may operate the fluid source 210 such that the fluid is delivered only through the first fluid delivery channel 205 and out the first outlet 208 or is delivered only through the second fluid delivery channel 206 and out the second outlet 209. When the fluid is delivered only through the first fluid delivery channel 205, the fluid exiting the first outlet 208 may proximally retract the optical fiber 202 relative to the sheath 201, thus increasing the distance between the first and second lenses 10, 12. On the other hand, when the fluid is delivered only through the second fluid delivery channel 206, the fluid exiting the second outlet 209 may distally advance the optical fiber 202 relative to the sheath 201, thereby decreasing the distance between the first and second lenses 10, 12. Therefore, a user may adjust the spot size and intensity of a laser beam emitted from the laser assembly 200 by simply controlling the fluid supplied to the sheath 201. Such a configuration may eliminate the need to manually adjust the relative position of the sheath 201 and the optical fiber 202.

The optical fiber 202 may also include a first hard stop 211 and a second hard stop 212. The first hard stop 211 may be disposed external the sheath 201 and may be configured to prevent distal advancement of the optical fiber 202 beyond a predetermined distance. For example, the first hard stop 211 may be appropriately positioned such that the first and second lenses 10, 12 may be prevented from contacting each other. The second hard stop 212 may be disposed within the sheath 201 and may be configured to prevent proximal retraction of the optical fiber 202 beyond a predetermined distance. For instance, the second hard stop 212 may be appropriately positioned such that the first lens 10 may be maintained distal the second outlet 209. In other words, proximal retraction of the optical fiber 202 may be restricted so that first lens 10 may not be moved proximal the second outlet 209. This may maintain the optical fiber 202 in an appropriate position such that the fluid exiting the second outlet 209 will distally advance the optical fiber 202. It should also be appreciated that either the first or second fluid delivery channel 205, 206 may be in communication with a vacuum source (not shown) to aspirate fluid buildup within the sheath 201.

As described in the prior embodiments, a spot size and an intensity of a laser beam may be adjusted via axial movement between the first lens 10 and the second lens 12. It should be appreciated, however, that in other embodiments, rotational movement between a plurality of lenses associated with the described laser assemblies, and perhaps having somewhat irregular lens characteristics including shape and surface features, may adjust the spot size and intensity of the laser beam. For example, a first focusing lens may be rotated in and out of alignment with a second focusing lens to adjust the intensity and spot size of an emitted laser beam. Such a configuration may also deflect and straighten the emitted laser beam.

It should also be appreciated that the distance between the first lens 10 and the second lens 12 may be adjusted by electrical means. For example, a material capable of electrical expansion and contraction may be associated with the optical fiber 5. An appropriate voltage may be supplied to the material to expand or contract the material. The electrical expansion or contraction of the material may advance or retract the optical fiber 5, and therefore, may adjust the distance between the first lens 10 relative to the second lens 12.

Any aspect set forth in any embodiment may be used with any other embodiment set forth herein. Every device and apparatus set forth herein may be used in any suitable medical procedure, may be advanced through any suitable body lumen and body cavity, and may be used for treatment of any suitable body portion. For example, the apparatuses and methods described herein may be used in any natural body lumen or tract, including those accessed orally, vaginally, or rectally.

The many features and advantages of the present disclosure are apparent from the detailed specification, and thus, it is intended by the appended claims to cover all such features and advantages of the present disclosure which fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

What is claimed is:

1. An apparatus, comprising:
   an optical fiber including a distal end and configured to emit a beam of energy;
   a first lens coupled to the distal end of the optical fiber; and
   a sheath including a channel and a second lens positioned on a distal region of the sheath,
   wherein the optical fiber is disposed within the channel of the sheath to permit relative movement between the first lens and the second lens and thereby adjust a beam of energy that exits the sheath,
   a first fluid delivery channel having an opening positioned in fluid communication with the channel of the sheath and between the first lens and second lens;
   a second fluid delivery channel having an opening positioned proximal of the first lens; and
   wherein the first lens and the second lens are arranged so that the beam of energy passes through the first lens and the second lens before exiting the distal region of the sheath.

2. The apparatus of claim 1, wherein the optical fiber is longitudinally slidably disposed within the channel.

3. The apparatus of claim 1, wherein an intensity of the beam of energy that exits the distal region of the sheath increases when a distance between the first lens and the second lens increases, and the intensity of the beam of energy decreases when the distance between the first lens and the second lens decreases.

4. The apparatus of claim 1, wherein a spot size of the beam of energy that exits the distal region of the sheath increases when a distance between the first lens and the second lens decreases, and the spot size decreases when the distance between the first lens and the second lens increases.

5. The apparatus of claim 1, wherein the first lens is fixedly attached to the distal end of the optical fiber, and the second lens is fixedly attached within the channel of the sheath so as to permit longitudinal relative movement between the first lens and the second lens.

6. The apparatus of claim 1, further comprising a stop coupled to the optical fiber and positioned external the channel of the sheath, wherein the stop is configured to limit distal advancement of the optical fiber.

7. The apparatus of claim 1, wherein fluid delivery to the first fluid delivery channel proximally retracts the optical fiber, and fluid delivery to the second fluid delivery channel distally advances the optical fiber.

8. The apparatus of claim 1, wherein the apparatus is a medical device.

9. The apparatus of claim 8, wherein the optical fiber and the sheath are flexible to traverse a tortuous anatomy in a body.

10. A method of transmitting a beam of energy from an apparatus, the apparatus including an optical fiber disposed within a sheath, the method comprising:
   transmitting a beam of energy through the optical fiber and through a first lens coupled to a distal end of the optical fiber;
   emitting the beam of energy out of the sheath through a second lens positioned on a distal region of the sheath to fragment or vaporize body tissue; and
   delivering fluid via at least one of a first fluid delivery channel or a second fluid delivery channel into the channel of the sheath so as to adjust the beam of energy that exits the sheath by moving the first lens relative to the second lens,
   wherein fluid delivery to the first fluid delivery channel proximally retracts the optical fiber, and fluid delivery to the second fluid delivery channel distally advances the optical fiber;
   wherein the beam of energy passes through the first lens and the second lens before exiting the distal region of the sheath.

11. The method of claim 10, further comprising increasing an intensity of the beam of energy that exits the sheath by increasing a longitudinal distance between the first lens and the second lens, and decreasing the intensity of the beam by decreasing the longitudinal distance between the first lens and the second lens.

12. The method of claim 10, wherein a spot size of the beam of energy that exits the sheath increases when a distance between the first lens and the second lens decreases, and the spot size decreases when the distance between the first and second lenses increases.

13. The method of claim 10, wherein moving the first lens and the second lens relative to each other includes longitudinally translating the optical fiber relative to the sheath.

14. The method of claim 10, further comprising directing the beam of energy from the apparatus towards tissue of a patient.

15. An apparatus, comprising:
   an optical fiber including a distal end and configured to emit a beam of energy;
   a first lens coupled to the distal end of the optical fiber;
   a sheath including a channel and a second lens fixedly coupled to a distal region of the sheath, and
   a first fluid delivery channel and a second fluid delivery channel, wherein the first fluid delivery channel includes an opening in fluid communication with the channel of the sheath and positioned between the first lens and the second lens, and wherein the second fluid delivery channel includes an opening in fluid communication with the channel of the sheath and positioned proximal of the first lens;
   wherein the optical fiber and the first lens are disposed within the channel of the sheath to permit relative longitudinal movement between the first lens and the second lens and thereby adjust a beam of energy that exits the sheath, and
   wherein the first lens and the second lens are arranged so that the beam of energy passes through the first lens and the second lens before exiting the distal region of the sheath.

16. The apparatus of claim 1, wherein the second lens is distal to the first lens, and the first lens is slidable relative to the sheath.

* * * * *